(12) United States Patent
Dickson et al.

(10) Patent No.: US 7,015,219 B2
(45) Date of Patent: Mar. 21, 2006

(54) 3-ARYL-HYDROXYBENZOXAZINES AND 3, 4-DIHYDRO-3-ARYL-HYDROXYBENZOXAZINES AS SELECTIVE ESTROGEN RECEPTOR BETA MODULATORS

(75) Inventors: John K. Dickson, Eastampton, NJ (US); Timur Gungor, Hopewell, NJ (US); Wu Yang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/322,689

(22) Filed: Dec. 18, 2002

(65) Prior Publication Data

US 2003/0195207 A1 Oct. 16, 2003

Related U.S. Application Data

(60) Provisional application No. 60/341,961, filed on Dec. 19, 2001.

(51) Int. Cl.
*C07D 498/06* (2006.01)
*C07D 295/26* (2006.01)
*C07D 295/192* (2006.01)
*A61K 31/538* (2006.01)
*A61K 31/5383* (2006.01)

(52) U.S. Cl. .................. 514/229.8; 544/101; 544/105; 514/230.5

(58) Field of Classification Search ............... 544/71, 544/105, 101; 514/229.8, 230.5
See application file for complete search history.

(56) References Cited

U.S. PATENT DOCUMENTS

| 3,711,478 A | 1/1973 | Imscher et al. |
| 4,411,890 A | 10/1983 | Momany ........... 424/177 |

FOREIGN PATENT DOCUMENTS

| WO | WO89/07110 | 8/1989 |
| WO | WO89/07111 | 8/1989 |
| WO | WO93/04081 | 3/1993 |
| WO | WO01/42186 | * 6/2001 |

OTHER PUBLICATIONS

Kuiper et al., Endocrinology, vol. 139, No. 10, 4252-4263.
The Practice of Medicinal Chemistry, Camille G. Wermuth et al., Chapter 31, 671-696 (Academic Press, 1996); Design of Prodrugs, edited by H. Bundgaard, (Elsevier, 1985).
Design of Prodrugs, edited by H. Bundgaard (Elsevier, 1985) (table of contents enclosed).
A Textbook of Drug Design and Development , P. Krogsgaard-Larson and H. Bundgaard, eds. Chapter 5, 113-191 (Harwood Academic Publishers, 1991).
Battistoni et al., Synthesis, 220-221, 1979.
Barnett et al., J.C.S. Perkin Trans. II, 747-755, 1979.
Atkinson et al., J. Org. Chem., 56, 1788-1800, 1991.
Allah et al., J. Heterocyclic Chem., 24, 1745-1748, 1987.
Edwards et al., Biorganic & Medicinal Chemistry Letters, 9, 1003-1008, 1999.
Hamann et al., J. Med. Chem., 42, 210-212, 1999.

* cited by examiner

*Primary Examiner*—Mark L. Berch
*Assistant Examiner*—Kahsay Habte
(74) *Attorney, Agent, or Firm*—Burton Rodney

(57) ABSTRACT

Substituted benzoxazine and 3,4-dihydrobenzoxazine derivatives possessing activity as estrogen receptor beta (ERβ) modulators are provided which have the structure of formula I

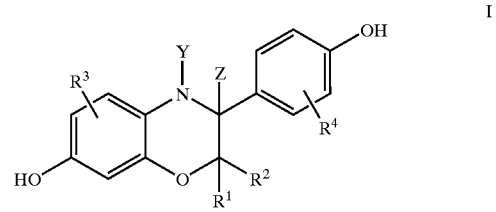

wherein the substitutents are as described herein.

In addition, a method is provided for preventing, inhibiting or treating the progression or onset of pathological conditions associated with the estrogen receptor and to pharmaceutical compositions containing such compounds.

8 Claims, No Drawings

3-ARYL-HYDROXYBENZOXAZINES AND 3,4-DIHYDRO-3-ARYL-HYDROXYBENZOXAZINES AS SELECTIVE ESTROGEN RECEPTOR BETA MODULATORS

This application claims priority from U.S. Provisional Application No. 60/341,961 filed Dec. 19, 2001 which is incorporated herein by reference.

FIELD OF THE INVENTION

The present invention relates to novel, substituted benzoxazine and 3,4-dihydrobenzoxazine compounds, methods of using such compounds in the treatment of estrogen receptor-associated conditions, such as bone disorders, for example osteoporosis, and to pharmaceutical compositions containing such compounds.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function and the protection of organ systems from the effects of aging. However, in addition to its positive effects, estrogen also is a potent growth factor in the breast and endometrium that increases the risk of cancer.

Until recently, it was assumed that estrogen binds to a single estrogen receptor (ER) in cells. However, a second estrogen receptor, ER beta (ERβ), has been identified and cloned, with the original ER being renamed ER alpha(ERα). *Endocrinology* 1998 139 4252–4263. ERβ and ERα share about a 50% identity in the ligand-binding domain and only 20% homology in their amino-terminal transactivation domain. The difference in the identity of the two ER subtypes accounts for the fact that small compounds may demonstrate a higher affinity to bind to one subtype over the other.

Further, ERβ and ERα are believed to have varied distributions and functions in different tissues. For example, in rats, ERβ is strongly expressed in brain, bone and vascular epithelium, but weakly expressed in uterus and breast, relative to ERα. Further, ERα knockout mice are sterile and exhibit little or no evidence of hormone responsiveness of reproductive tissues. In contrast, ERβ knockout mice are fertile and exhibit normal development and function of breast and uterine tissue. These observations suggest that selectively targeting ERβ over ERα could confer beneficial effects in several important diseases, such as Alzheimer's disease, anxiety disorders, depressive disorders, osteoporosis and cardiovascular diseases, without the liability of reproductive system side effects. Selective effects on ERβ expressing tissues over uterus and breast could be achieved by agents that selectively interact with ERβ over ERα.

Accordingly, it would be advantageous to develop a series of novel compounds, which selectively modulate ERβ receptors and may be employed to treat a variety of estrogen-dependent pathological conditions.

SUMMARY OF THE INVENTION

In accordance with the present invention, substituted benzoxazine and 3,4-dihydrobenzoxazine derivatives are provided which have the structure of formula I

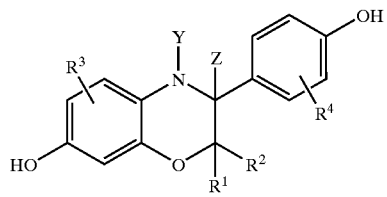

wherein
$R^1$ and $R^2$ are each independently selected from the group consisting of hydrogen, substituted or unsubstituted alkyl, substituted or unsubstituted aryl, substituted or unsubstituted cycloalkylalkyl, substituted or unsubstituted arylalkyl and hydroxyalkyl, or $R^2$ together with $R^4$ may independently be cyclized to form —$(CH_2)_n$— where n=1, 2, or 3;
$R^3$ is selected from the group consisting of hydrogen, OH, halo, $CF_3$, CN, substituted or unsubstituted alkyl, substituted or unsubstituted alkenyl, substituted or unsubstituted alkynyl and alkoxy;
$R^4$ is selected from the group consisting of hydrogen, substituted or unsubstituted alkyl, halo, OH and alkoxy;
Z is hydrogen, or Y and Z can together form a bond;
Y, where Z is H, is selected from the group consisting of hydrogen, substituted or unsubstituted alkyl, $COR^5$, $CSR^5$, $SO_2R^5$, $CONR^6R^7$, $COOR^8$ and $COSR^9$, or Y together with $R^3$ may form a six membered heterocyclic ring containing —$OCH_2CH_2$— or —$OCH_2CO$—;
$R^5$ is substituted or unsubstituted alkyl or substituted or unsubstituted aryl;
$R^6$ and $R^7$ are each independently hydrogen, substituted or unsubstituted alkyl or substituted or unsubstituted aryl; and
$R^8$ and $R^9$ are each independently substituted or unsubstituted alkyl or substituted or unsubstituted aryl.

The compounds of formula I above further include all pharmaceutically acceptable salts, stereoisomers and prodrug esters of formula I.

The compounds of formula I modulate the function of the estrogen receptor beta (ERβ) and include compounds which are, for example, selective agonists, partial agonists, antagonists or partial antagonists of the ERβ. Consequently, the compounds of the present invention may be used in the treatment of multiple diseases or disorders associated with ERβ activity, such as the treatment of bone disorders, cardiovascular diseases, hypercholesterolemia, hypertriglyceridemia, vasomotor disorders, urogenital disorders, prostatic hypertrophy, endometrial hyperplasia and cancer. Further, the compounds of the present invention may have central nervous system (CNS) action and therefore may be useful for the treatment of multiple CNS disorders, such as neurodegenerative diseases.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

In addition, a method is provided for preventing, inhibiting or treating the onset of pathological conditions associated with the estrogen receptor, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human patient in need of treatment.

Preferred are compounds of formula I having the structure Ia:

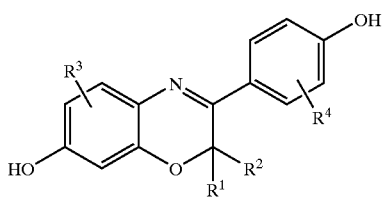

wherein
$R^1$ is alkyl;
$R^2$ is hydrogen;
$R^3$ is hydrogen, alkyl or OH; and
$R^4$ is hydrogen, alkyl, halo, OH or alkoxy.

Further embodiments include compounds formula I having the structure Ia wherein
$R^1$ is alkyl;
$R^2$ is hydrogen;
$R^3$ is alkyl or OH; and
$R^4$ is hydrogen, alkyl, halo, OH or alkoxy.

DETAILED DESCRIPTION OF THE INVENTION

The following abbreviations are employed herein:
Ac=acetyl
DMF=N,N-dimethylformamide
Et=ethyl
EtOAc=ethyl acetate
HPLC=high performance liquid chromatography
LAH=lithium aluminum hydride
LC/MS=high performance liquid chromatography/mass spectrometry
Me=methyl
meq=milliequivalent(s)
mg=milligram(s)
M+H=parent plus a proton
min=minute(s)
ml=milliliter(s)
mmol=millimole(s)
MS or Mass Spec=mass spectrometry
NMR=nuclear magnetic resonance
Pd/C=palladium on carbon
Pr=propyl
rt=room temperature
THF=tetrahydrofuran
TFA=trifluoroacetic acid The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form groups such as trifluoro methyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain. "Substituted alkenyl" includes an alkenyl group optionally substituted with 1 or more substituents, such as those described above for alkyl.

As used herein, the term "alkynyl" refers to straight or branched chain radicals of 2 to 20 carbons, preferably 2 to 12 carbons and more preferably 2 to 8 carbons in the normal chain, which include one or more triple bonds in the normal chain. "Substituted alkynyl" includes an alkynyl group optionally substituted with 1 or more substituents, such as those described above for alkyl.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

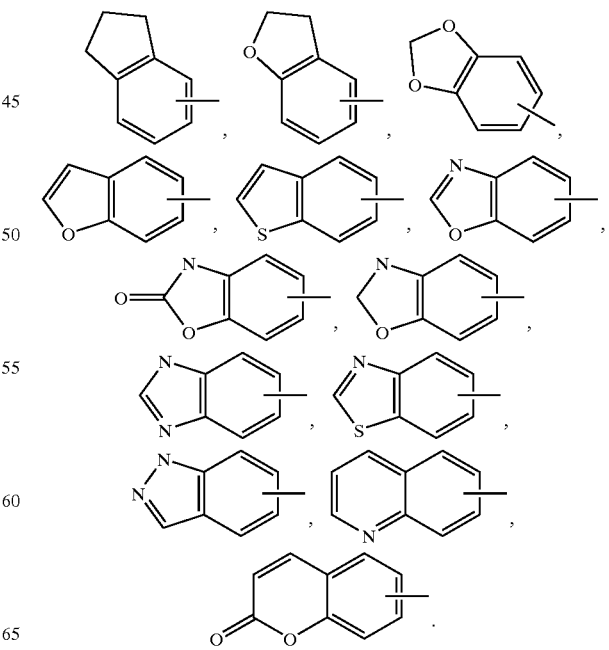

"Substituted aryl" includes an aryl group optionally substituted with 1 or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, and/or any of the alkyl substituents set out herein.

Unless otherwise indicated, the term "cycloalkyl" as employed herein alone or as part of another group includes saturated or partially unsaturated (containing 1 or more double bonds) cyclic hydrocarbon groups containing from 3 to 8 carbons. Representative examples of cycloalkyl include, cyclopropyl, cyclobutyl, cyclopentyl and cyclohexyl. "Substituted cycloalkyl" includes a cycloalkyl group optionally substituted with 1 or more substituents such as those described above for alkyl and/or aryl.

The term "cycloalkylalkyl," as used herein, refers to a cycloalkyl group appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like. "Substituted cycloalkylalkyl" includes a cycloalkylalkyl group optionally substituted with 1 or more substituents such as those described above for alkyl and/or aryl.

The term "arylalkyl" as used alone or as part of another group refer to an alkyl group, as defined herein, having an aryl substituent, as defined herein. Representative examples of arylalkyl include, but are not limited to, benzyl, 2-phenylethyl, 3-phenylpropyl, and the like. "Substituted arylalkyl" includes an arylalkyl group optionally substituted with 1 or more substituents such as those described above for alkyl and/or aryl.

"Hydroxyalkyl" groups are alkyl groups that have a hydroxyl group appended thereto.

The term "alkoxy" denotes —OR, wherein R is alkyl, as defined herein.

As used herein, the term "halo" or "halogen" refers to fluorine, chlorine, bromine and iodine.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry,* Camille G. Wermuth et al., Ch 31, (Academic Press, 1996);

b.) *Design of Prodrugs,* edited by H. Bundgaard, (Elsevier, 1985); and c.) *A Textbook of Drug Design and Development,* P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl-or p-toluene-sulfonic acid. Corresponding acid addition salts can also be formed having, if desired, an additionally present basic center.

Preferred salts of the compounds of formula I which contain a basic group include monohydrochloride, hydrogensulfate, methanesulfonate, phosphate or nitrate.

Where the compounds of formula I are in acid form they may form a pharmaceutically acceptable salt, such as alkali metal salts, such as lithium, sodium or potassium, alkaline earth metal salts, such as calcium or magnesium, as well as zinc or aluminum and other cations, such as ammonium, chlorine, diethanolamine, lysine (D or L) ethylenediamine, tris-(hydroxymethyl)aminomethane (TRIS), n-methyl glucosamine (NMG), triethanolamine and dehydroabietylamine.

Where the compounds of formula I are phenols, they may form a pharmaceutically acceptable salt, such as alkali metal salts, such as lithium, sodium or potassium, alkaline earth metal salts, such as calcium or magnesium, as well as zinc or aluminum and other cations.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods, for example, chromatographic or fractional crystallization.

The compounds of the formula I of the invention may be prepared as shown in the following reaction schemes and description thereof, as well as relevant published literature procedures that may be used by one skilled in the art. Exemplary reagents and procedures for these reactions appear hereinafter and in the working Examples.

Where Y is an alkyl group, compounds of formula II can be prepared by direct alkylation of compounds of formula III with alkyl halides or alternatively, by reductive amination of compounds of formula III with aldehydes. Where Y is a $COR^5$ or $SO_2R^5$ group, compounds of formula II can be prepared by treatment of compounds of formula III with acid chlorides or sulfonyl chlorides. Where Y is a $CONR^6R^7$, $COOR^8$ or $COSR^9$ group, compounds of formula II can be prepared by treatment of a common intermediate of formula IIIa with nucleophiles such as amines, alcohols and thiols. Compounds of formula Ib where Y is hydrogen can be

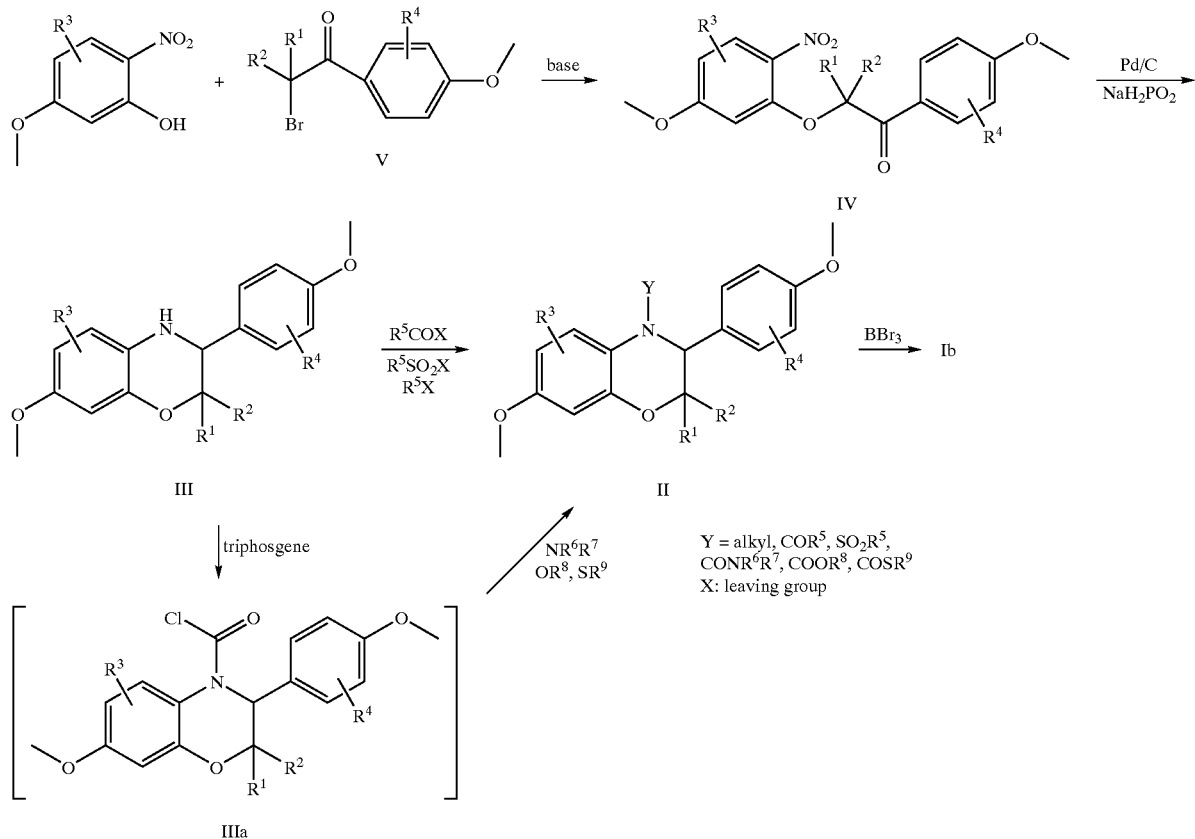

SCHEME 1

Compounds of formula Ib, shown below, can be prepared as illustrated in Scheme 1, by treatment of compounds of formula II with excess of $BBr_3$ or alternatively in some cases with pyridine HCl at high temperature. Compounds of formula Ib represent compounds of formula I where Z is hydrogen

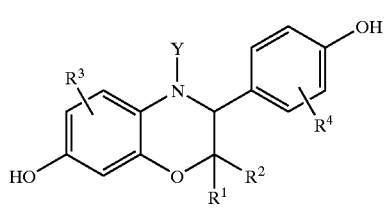

Ib prepared from the treatment of compounds of formula III with excess $BBr_3$. Intermediate IIIa can be prepared by treatment of compounds of formula III with triphosgene and can be used without purification.

Compounds of formula III can be prepared by reduction of compounds of formula IV with $NaH_2PO_2$ in the presence of Pd/C as the catalyst (Battistoni, P., Bruni, G. F. *Synthesis*, 1979, 220–221).

Compounds of formula IV can be prepared by alkylation of substituted 3-methoxy-6-nitrophenols with compounds of formula V. Substituted 3-methoxy-6-nitrophenols can be prepared by nitration of substituted dimethoxybenzenes followed by demethylation with $BBr_3$ (*J. C. S Perkin Trans. II* 1979, 747; *J. Org. Chem.* 1991, 56, 1788). Compounds of formula V can be prepared by treatment of substituted acetophenones with a brominating agent, such as $Br_2$ in chloroform (*J. Heterocyl. Chem.* 1987, 24, 1745).

SCHEME 2

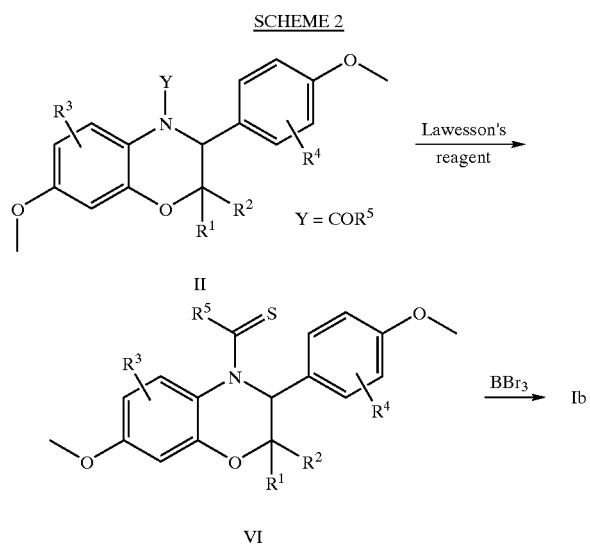

Where Y is a CSR$^5$ group, compounds of formula Ib can be prepared as shown in Scheme 2, by treatment of compounds of formula VI with excess of BBr$_3$. Compounds of formula VI can be prepared by treatment of compounds of formula II (from Scheme 1) with a sulfating agent, such as Lawesson's reagent.

SCHEME 3

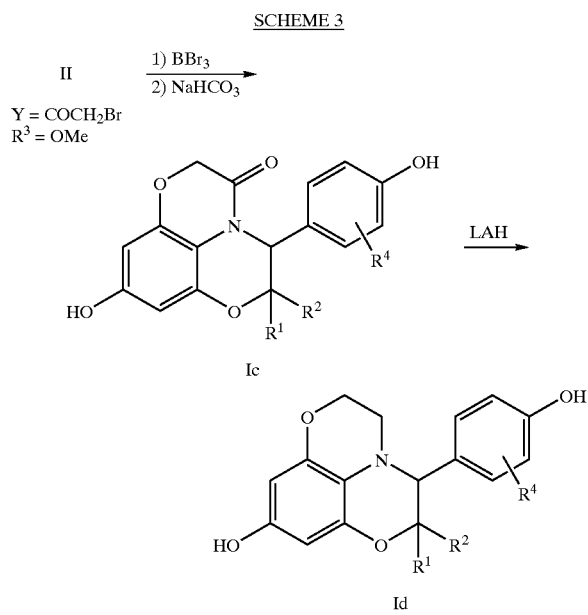

Compounds of formula Id can be prepared as shown in Scheme 3 by reduction of compounds of formula 1c with a reducing agent, such as lithium aluminum hydride. Compounds of formula Id represent compounds of formula I wherein R$^3$ is cyclized with Y to form a six-membered heterocycle containing —OCH$_2$CH$_2$—.

Compounds of formula Ic can be prepared by deprotection of compounds of formula II (from Scheme 1) where Y is COCH$_2$Br and R$^3$ is 5-OMe, via treatment with BBr$_3$ followed by a base, such as NaHCO$_3$. Compounds of formula Ic represent compounds of formula I wherein R$^3$ is cyclized with Y to form a six-membered heterocycle containing —OCH$_2$CO—.

SCHEME 4

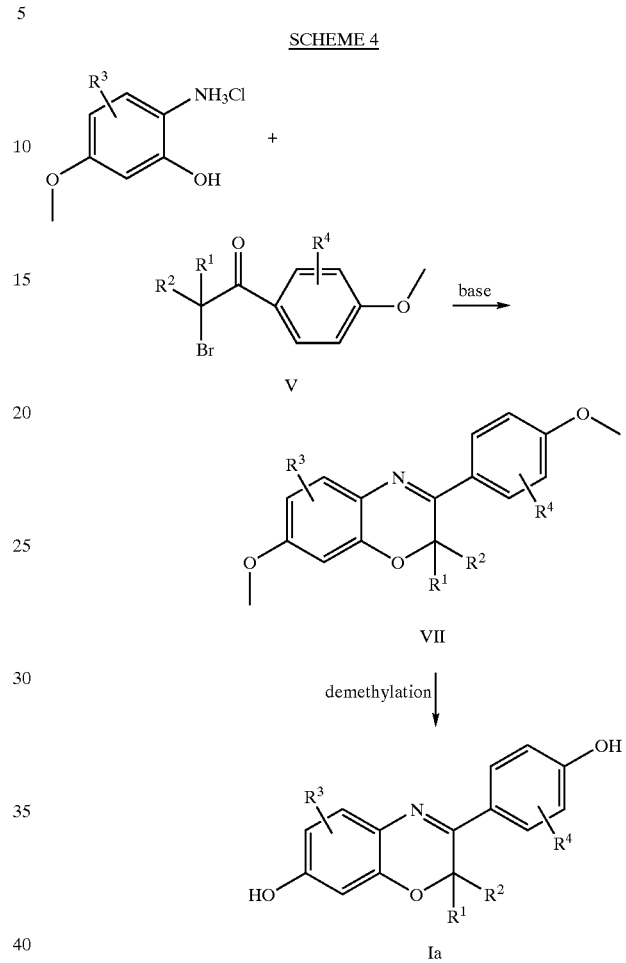

Compounds of formula Ia can be prepared as shown in Scheme 4, by standard demethylation of compounds of formula VII with, for example, BBr$_3$. Compounds of formula Ia represent compounds of formula I where Z together with Y form a bond.

Compounds of formula VII can be prepared by treatment of substituted 3-methoxy-6-aminophenols with compounds of formula V in the presence of a base (*J. Indian Chem.* 1989, 138).

Utility & Combinations

A. Utilities

The compounds of the present invention modulate the function of the estrogen receptor beta (ERβ), and include compounds which are, for example, selective agonists, partial agonists, antagonists or partial antagonists of the ERβ. Thus, the present compounds are useful in the treatment of a condition or disorder which can be treated by modulating the function or activity of an ERβ in a subject, wherein treatment comprises prevention, partial alleviation or cure of the condition or disorder. Modulation may occur locally, for example, within certain tissues of the subject, or more extensively throughout a subject being treated for such a condition or disorder.

Accordingly, the compounds of the present invention can be administered to mammals, preferably humans, for the treatment of a variety of conditions and disorders, including, but not limited to bone disorders, e.g., osteoporosis (including glucocorticoid-induced osteoporosis), osteopenia, Paget's disease and peridontal disease; cardiovascular diseases (including fibroproliferative conditions); hypercholesterolemia; hypertriglyceridemia; vasomotor disorders (e.g., hot flashes); urogenital disorders (e.g., urinary incontinence); prostatic hypertrophy; endometrial hyperplasia; and cancer, including prostate cancer, uterine cancer, ovarian cancer, breast cancer and endometrial cancer. Further, the compounds of)the present invention may have central nervous system action and therefore may be useful for the treatment of multiple CNS disorders, such as neurodegenerative diseases (e.g., improvement of cognitive function and the treatment of dementia, including Alzheimer's disease and short-term memory loss).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination with other modulators of the estrogen receptor beta and/or with other suitable therapeutic agents useful in the treatment of the aforementioned disorders such as, but not limited to, anti-osteoporosis agents, cholesterol lowering agents, growth promoting agents, modulators of bone resorption and cardiovascular agents.

Examples of suitable anti-osteoporosis agents for use in combination with the compounds of the present invention include bisphosphonates (e.g., alendronate, risedronate, ibandronate and zolendrate), parathyroid hormone, PTH fragments and PTH analogues (e.g. PTH-(1–84), PTH-(1–34)) and calcitonins.

Examples of suitable cholesterol lowering agents for use in combination with the compounds of the present invention include HMG-CoA reductase inhibitors (e.g., pravastatin, lovastatin, atorvastatin, simvastatin, NK-104 (a.k.a. itavastatin, nisvastatin or nisbastatin) and ZD-4522 (a.k.a. rosuvastatin, atavastatin or visastatin)), MTP inhibitors, fibrates (e.g., gemfibrozil) and bile acid sequestrants.

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-HTD agonists, such as sumatriptan, or agents which inhibit somatostatin or its release, such as physostigmine and pyridostigmine.

Examples of suitable modulators of bone resorption for use in combination with the compounds of the present invention include estrogen; selective estrogen receptor modulators (e.g., tamoxifen, lasofoxifene, TSE-424 and raloxifene); selective androgen receptor modulators, such as those disclosed in Edwards, *Bio. Med. Chem. Let.*, 1999 9, 1003–1008 and *J. Med. Chem.*, 1999 42, 210–212; hormone replacement therapies; vitamin D and analogues thereof (e.g., 1,25-dihydroxy vitamin D3); elemental calcium and calcium supplements; cathepsin K inhibitors; chloride channel inhibitors (e.g., ClC-7 inhibitors); MMP inhibitors; vitronectin receptor antagonists; Src $SH_2$ antagonists; Src kinase inhibitors; vacular $H^+$-ATPase inhibitors; osteoprotegrin; Tibolone; p38 inhibitors; prostanoids; PPAR gamma antagonists or isoflavinoids (e.g., genistein and ipriflavone); androgens (e.g., testosterone and dihydrotestosterone); RANK ligand antagonists; TRAP inhibitors; AP-1 inhibitors and progesterone receptor agonists (e.g., medroxyprogesterone acetate (MPA)).

Examples of suitable cardiovascular agents for use in combination with the compounds of the present invention include vasopeptidase inhibitors, ACE inhibitors, α-reductase inhibitors, muscarinic Ach antagonists, acetylcholinesterase inhibitors, angiotensin II receptor antagonists, thrombin inhibitors, Factor Xa inhibitors, tissue plasminogen activators, streptokinase, or other thrombolytic or antithrombotic agents.

Compounds of formula I and their physiologically acceptable salts, prodrug esters or stereoisomers thereof may be formulated for administration via any suitable means, for example, orally, such as in the form of tablets, capsules, granules or powders; rectally, such as in the form of suppositories; nasally, including administration to the nasal membranes, such as by inhalation spray; topically (including buccal and sublingual); vaginal or parental (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well known in the art of pharmacy. All methods may include the step of bringing into association the active compound with liquid carriers or finely divided solid carries, or both, and then if necessary, shaping the product into the desired formulation.

The active principle may be in the form of a solid or a liquid and can be utilized in a composition such as tablet, capsule, ointment, solution or suspension, or in other suitable carrier materials. Examples of suitable carrier materials are iontophoetic devices, rectal suppositories, transderman systems, granules, injectable preparations, or the like, prepared according to procedures known in the art. Further, the active principle comprising a pharmaceutically effective amount of at least one compound of formula I, either alone or in combination, or in combination with one or more other active agent(s) may be incorporated with excipients normally employed in therapeutic medicines, such as talc, gum arabic, lactose, starch, magnesium stearate, polyuidone, cellulose derivatives, cacao butter, semisynthetic glycerides, aqueous or non-aqueous vehicles, fats of animal or vegetable origin, glycols, various wetting agents, dispersants or emulsifiers, silicone gels, stabilizers, certain polymers or copolymers, preservatives, binders, flavorings, colors and the like, as called for by acceptable pharmaceutical practice.

Dosage of the active principle required for use in treatment may vary not only with the particular compound selected, but also with the route of administration, the nature of the condition being treated and the age and condition of the patient. In general, however, a suitable dose will be in the range of from about 0.0002 to 300 mg/kg of body weight per day, particularly from about 0.02 to 50 mg/kg of body weight per day, on a regimen of single or 2 to 4 divided daily doses. For example, for an adult with an average weight of 60 to 70 Kg, the dosage of active principle can vary between 1 and 500 mg when administered orally, in one or more daily doses, or from 0.01 to 50 mg, when administered parenterally in one or more daily dosages.

The above other therapeutic agents, when employed in combination with the compounds of the present invention, may be used, for example, in those amounts indicated in the Physicians' Desk Reference (PDR) or as otherwise determined by one of ordinary skill in the art.

The following working examples serve to better illustrate, but not limit some of the preferred embodiments of the present invention.

All temperatures are expressed in degrees centigrade unless otherwise indicated. Standard analytical HPLC condition: YMC S5 ODS column (4.6×50 mm), 0–100% B:A (solvent A=90% $H_2O$/MeOH+0.2% $H_3PO_4$; solvent B=90% MeOH/$H_2O$+0.2% $H_3PO_4$), linear gradient over 4 minutes at 1 ml/min, detection at 220 nM.

EXAMPLE 1

3,4-dihydro-3-(4-hydroxyphenyl)-2H-1,4-benzoxazine-5,7-diol

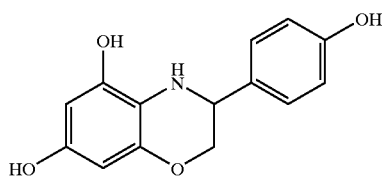

Compound 1a:

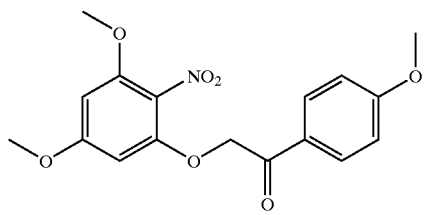

A solution of 2-nitro-3,5-dimethoxyphenol (420 mg, 2.11 mmol) in acetone (6.5 ml) was treated with anhydrous $K_2CO_3$ (583 mg, 4.22 mmol), followed by addition of α-bromo-4'-methoxyacetophenone (532 mg, 2.32 mmol) under an argon atmosphere. The reaction mixture turned immediately to a dark brownish color and was allowed to stir overnight at rt. The reaction mixture was then filtered and the filtrate was concentrated and flash chromatographed (silica gel, 33% EtOAc/Hexanes) to afford 400 mg (55%) of compound 1a as a yellow solid.

HPLC retention time=2.94 min. $^1$H NMR (CDCl$_3$, 400 MHz) δ 7.97 (d, J=8.8 Hz, 2H), 6.95 (d, J=8.8 Hz, 2H), 6.12 (d, J=2.6 Hz, 1H), 6.04 (d, J=2.6 Hz, 1H), 5.21 (s, 2H), 3.88 (s, 3H), 3.84 (s, 3H), 3.77 (s, 3H).

Compound 1b:

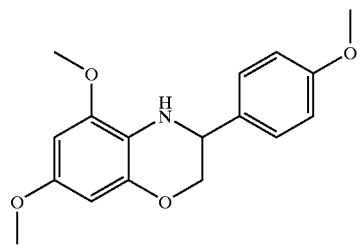

A solution of compound 1a (400 mg, 1.15 mmol) in THF/$H_2O$ (8 ml each) was treated with NaH$_2$PO$_2$ (800 mg, 9.09 mmol) and degassed. Pd/C (10%, 20 mg) was added under an argon atmosphere. The reaction mixture was allowed to stir at rt overnight, then filtered and the filtrate was diluted with $H_2O$(40 ml) and extracted with ether (2×40 ml). The combined ether layers were washed with brine (20 ml), dried over MgSO$_4$, filtered and concentrated in vacuo to give a dark red oil. Purification by flash chromatography (silica gel, 33% EtOAc/Hexanes) afforded 180 mg (52%) of compound 1b as a yellow solid along with 120 mg(30%) of compound 1a.

LC/MS (ESI) (M+H)$^+$=302. HPLC retention time=3.00 min. $^1$H NMR (CDCl$_3$, 400 MHz) δ 7.35 (d, J=8.8 Hz, 2H), 6.91 (d, J=8.8 Hz, 2H), 6.13 (s, 2H), 4.34 (brd, J=8.4 Hz, 1H), 4.25 (ddd, J=10.5, 2.6, 2.2 Hz, 1H), 4.04–3.99 (m, 2H), 3.82 (s, 3H), 3.81 (s, 3H), 3.75 (s, 3H).

Compound 1b (57 mg, 0.17 mmol) was dissolved in CH$_2$Cl$_2$ (1 ml) and was treated with 1N HCl in ether (0.17 ml, 0.17 mmol). The solvent was removed to give a yellow solid. To a suspension of this solid in anhydrous CH$_2$Cl$_2$ (2 ml) was added BBr$_3$ (319 μl, 3.38 mmol) at −15° C. The reaction mixture was warmed to 0° C. and stirred at 0° C. for three hours. The reaction was quenched by pouring the reaction mixture into a mixture of cold EtOAc/saturated NaHCO$_3$ (15 ml each). The aqueous layer was separated and extracted again with EtOAc$_3$ (25 ml). The combined EtOAc layers were washed with brine (15 ml), dried over MgSO$_4$, concentrated and flash chromatographed (silica gel, 33% EtOAc/Hexanes) to afford 15 mg (34%) of the title compound as a white foam.

LC/MS (ESI) (M+H)$^+$=260. HPLC retention time=1.26 min. $^1$H NMR (CD$_3$OD, 400 MHz) δ 7.24 (d, J=8.4 Hz, 2H), 6.78 (d, J=8.4 Hz, 2H), 5.95 (d, J=2.2 Hz, 1H), 5.85 (d, J=2.2 Hz, 1H), 4.22 (dd, J=2.6, 8.8 Hz, 1H), 4.15 (dd, J=3.0, 10.6 Hz, 1H), 3.91 (dd, J=8.8, 10.6 Hz, 1H).

EXAMPLE 2

3,4-dihydro-3-(4-hydroxyphenyl)-4-(1-oxopropyl)-2H-1,4-benzoxazine-5,7-diol

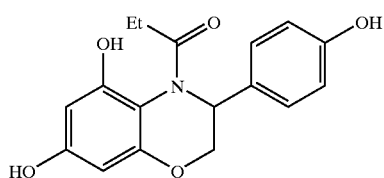

Compound 2a:

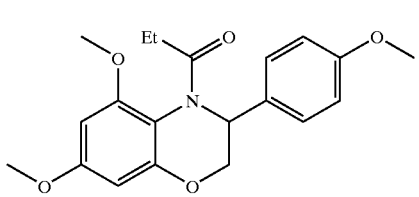

To a solution of compound 1b (99 mg, 0.33 mmol) in pyridine (0.5 ml), was added propionyl chloride (43 μl, 4.22 mmol) at 0° C. under nitrogen. A white precipitate formed immediately. The reaction mixture was allowed to warm to rt and stir overnight. Subsequently, the reaction mixture was diluted with EtOAc (30 ml), washed with 1N HCl (2×15 ml), brine (15 ml), dried over MgSO$_4$, concentrated and flash chromatographed (silica gel, 33% EtOAc/Hexanes) to afford 77 mg (66%) of compound 2a as a slightly yellowish foam.

LC/MS (ESI) (M+H)$^+$=358. HPLC retention time=3.21 min. $^1$H NMR (CDCl$_3$, 400 MHz) δ 7.19 (d, J=8.8 Hz, 2H), 6.73 (d, J=8.8 Hz, 2H), 6.11 (br s, 1H), 6.01 (s, 2H), 4.81 (dd, J=1.4, 11.5 Hz, 1H), 4.39 (dd, J=3.9, 11.5 Hz, 1H), 3.75 (s, 3H), 3.70 (s, 3H), 3.68 (s, 3H), 2.57 (m, 1H), 2.29 (m, 1H), 1.14 (t, J=7.5 Hz, 3H).

To a solution of compound 2a (77 mg, 0.22 mmol) in anhydrous CH$_2$Cl$_2$ (1.5 ml) was added BBr$_3$ (408 μl, 4.3 mmol) at −15° C. under nitrogen. The reaction mixture immediately turned a brownish color and was allowed to warm to rt and stir for 6 hours. Thereafter, the reaction was quenched by pouring the reaction mixture into a mixture of cold EtOAc/saturated NaHCO$_3$(15 ml each). The aqueous layer was separated and extracted again with EtOAc (25 ml). The combined EtOAc layers were washed with brine (15 ml), dried over MgSO$_4$, concentrated and flash chromatographed (silica gel, 5% MeOH/CH$_2$Cl$_2$) to afford 36 mg (53%) of the title compound as a white foam.

LC/MS (ESI) (M+H)$^+$=316. HPLC retention time=2.00 min. $_1$H NMR (CD$_3$OD, 400 MHz) δ 7.11 (d, J=8.4 Hz, 2H), 6.63 (d, J=8.4 Hz, 2H), 5.94 (S, 1H), 5.90 (s, 1H), 5.79 (s, 1H), 4.71 (d, J=11.4 Hz, 1H), 4.33 (dd, J=4.0, 11.4 Hz, 1H), 2.71 (m, 1H), 2.40 (m, 1H), 1.11 (t, J=7.5 Hz, 3H).

EXAMPLE 3

3,4-dihydro-3-(4-hydroxyphenyl)-4-methyl-2H-1,4-benzoxazine-5,7-diol hydrochloride salt

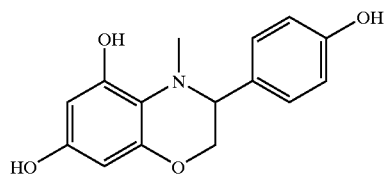

Compound 3a:

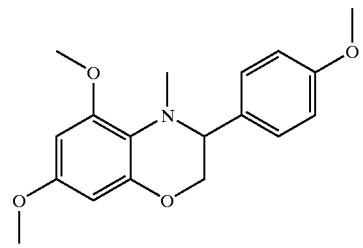

To a solution of compound 1b (103 mg, 0.34 mmol) in DMF, was added sodium hydroxide (58 mg, 1.45 mmol) and methyl iodide (65 ml, 1.04 mmol). The resulting mixture was allowed to stir at rt overnight and thereafter the reaction was quenched by addition of saturated NH$_4$Cl (10 ml). The reaction mixture was extracted with EtOAc. The EtOAc layer was washed with H$_2$O, brine, dried over MgSO$_4$, filtered and concentrated in vacuo to give a brownish oil. Purification by flash chromatography (silica gel, 20% EtOAc/Hexanes) afforded 25 mg (23%) of compound 3a as a colorless oil.

HPLC retention time=2.59 min. $^1$H NMR (CDCl$_3$, 400 MHz) δ 7.24(d, J=8.8 Hz, 2H), 6.82 (d, J=8.8 Hz, 2H), 6.16 (d, J=2.8 Hz, 1H), 6.06 (d, J=2.8 Hz, 1H), 4.22 (m, 2H), 4.07 (d, J=4.4 Hz, 1H), 3.87 (s, 3H), 3.76 (s, 3H), 3.72 (s, 3H), 2.79 (s, 3H).

Per the procedure described for the preparation of the Example 1 compound, compound 3a (33 mg, 0.094 mmol) was demethylated to provide the title compound (12 mg, 41%) as an off-white foam.

LC/MS (ESI) (M+H)$^+$=274. HPLC retention time=1.27 min. $^1$H NMR (CD$_3$OD, 400 MHz) δ 7.12 (d, J=8.8 Hz, 2H), 6.69 (d, J=8.8 Hz, 2H), 6.08 (d, J=2.2, 1H), 5.88 (d, J=2.2, 1H), 4.17 (m, 2H), 3.98 (m, 1H), 2.69 (s, 3H).

EXAMPLE 4

2,3-dihydro-5,7-dihydroxy-3-(4-hydroxyphenyl)-N-methyl-4H-1,4-benzoxazine-4-carboxamide

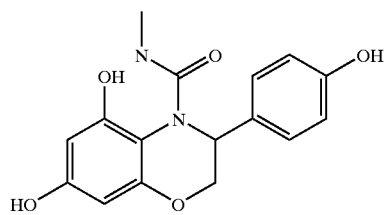

Compound 4a:

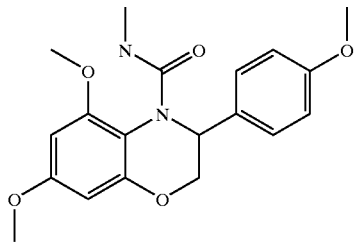

To a solution of compound 1b (67 mg, 0.22 mmol) and diisopropylethylamine (116 µl, 0.66 mmol) in anhydrous CH$_2$Cl$_2$ (1.0 ml), was added 20% phosgene in toluene (380 µl, 0.66 mmol) at rt. The reaction mixture immediately turned to light brownish color and was allowed to stir overnight at rt. Thereafter, the reaction mixture was diluted with EtOAc (20 ml). The resulting EtOAc mixture was washed with H2O, brine, dried over MgSO$_4$, filtered and concentrated in vacuo to give a yellow solid. This solid was redissolved in THF (1 ml) and cooled to 0° C. To this solution was added diisopropylethylamine (51 µl, 0.30 mmol) followed by addition of methylamine in THF (2M, 133 µl, 0.27 mmol). A white precipitate was immediately formed. The reaction mixture was slowly warmed overnight to rt, then concentrated and flash chromatographed (silica gel, 50% to 66% EtOAc/Hexanes) to afford 60 mg (75%) of compound 4a as a white foam.

HPLC retention time=2.78 min. $^1$H NMR (CDCl$_3$, 400 MHz) δ 7.23 (d, J=8.8 Hz, 2H), 6.73 (d, J=8.8 Hz, 2H), 6.05 (d, J=2.6 Hz, 1H), 6.01 (d, J=2.6 Hz, 1H), 5.88 (d, J=2.6 Hz, 1H), 5.29 (t, J=4.4 Hz, 1H), 4.84 (dd, J=1.3, 11.4 Hz, 1H), 4.40 (dd, J=3.5, 11.4 Hz, 1H), 3.81 (s, 3H), 3.71 (s, 3H), 3.68 (s, 3H), 2.85 (d, J=4.8 Hz, 3H).

Per the procedure described for the preparation of the Example 2 compound, compound 4a (55 mg, 0.153 mmol) was demethylated to provide the title compound (33 mg, 68%) as a white foam.

HPLC retention time=1.50 min. LC/MS (ESI) (M+H)$^+$ =317. $^1$H NMR (CD$_3$OD, 400 MHz) δ 7.14 (d, J=8.4 Hz, 2H), 6.62 (d, J=8.4 Hz, 2H), 5.94 (d, J=2.6 Hz, 1H), 5.76 (d, J=2.6 Hz, 1H), 5.62 (brs, 1 H), 4.77 (dd, J=11.0, 1.3 Hz, 1H), 4.24 (dd, J=11.0, 3.5 Hz, 1H), 2.80 (s, 3H).

EXAMPLE 5

3,4-dihydro-3-(4-hydroxyphenyl)-4-(1-thioxoethyl)-2H-1,4-benzoxazine-5,7-diol

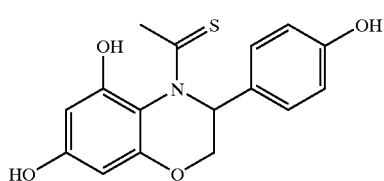

Compound 5a:

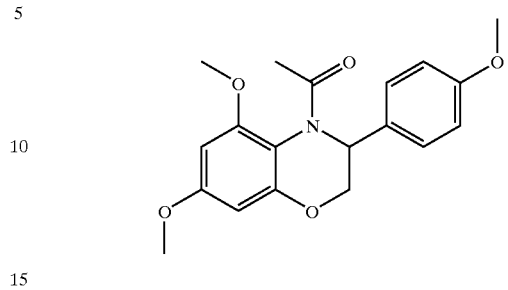

Per the procedure described for the preparation of compound 2a, compound 1b (80 mg, 0.266 mmol) was acetylated with acetyl chloride (28 µl, 0.4 mmol) to provide compound 5a (91 mg, 100%) as a pale yellow foam.

LC/MS (ESI) (M+H)$^+$=344. HPLC retention time=3.01 min. $^1$H NMR (CDCl$_3$, 400 MHz) δ 7.19 (d, J=8.8 Hz, 2H), 6.74 (d, J=8.8 Hz, 2H), 6.11 (br s, 1H), 6.02 (m, 2H), 4.81 (d, J=10.1 Hz, 1H), 4.43 (dd, J=3.9, 10.9 Hz, 1H), 3.77 (s, 3H), 3.72 (s, 3H), 3.70 (s, 3H), 2.15 (s, 3H).

Compound 5b:

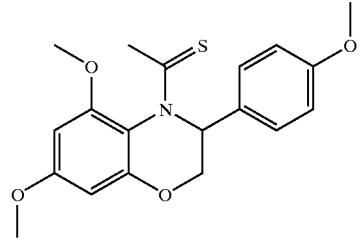

A solution of compound 5a (37 mg, 0.11 mmol) and Lawesson's reagent (65 mg, 0.16 mmol) in toluene (1 ml) was refluxed for 3 hours. Subsequently, the solution was concentrated and flash chromatographed (silica gel, 25% EtOAc/Hexanes) to afford 30 mg (77%) of compound 5b as a white foam.

HPLC retention time=3.53 min. $^1$H NMR (CDCl$_3$, 400 MHz) δ 7.32 (d, J=4.0 Hz, 1H), 7.21 (d, J=8.8 Hz, 2H), 6.73 (d, J=8.8 Hz, 2H), 6.02 (d, J=2.4 Hz, 1H), 5.96 (d, J=2.4 Hz, 1H), 4.93 (d, J=11.8 Hz, 1H), 4.55 (dd, J=4.0, 11.8 Hz, 1H), 3.73 (s, 3H), 3.72 (s, 3H), 3.70 (s, 3H), 2.69 (s, 3H).

Per the procedure described for the preparation of the Example 2 compound, compound 5b (30 mg, 0.153 mmol) was demethylated to provide the title compound (19 mg, 72%) as a white foam.

HPLC retention time=2.48 min. LC/MS (ESI) (M+H)$^+$ =318. $^1$H NMR (CD$_3$OD, 400 MHz) δ 7.06 (br d, J=3.5 Hz, 1H), 7.02 (d, J=8.3 Hz, 2H), 6.52 (d, J=8.3 Hz, 2H), 5.73 (d, J=2.6 Hz, 1H), 5.68 (d, J=2.6 Hz, 1H), 4.80 (1H), 4.32 (dd, J=14.4, 11.9 Hz, 1H), 2.60 (s, 3H).

EXAMPLE 6

2,3,5,6-tetrahydro-3-(4-hydroxyphenyl)-<1,4>ox-azino<4,3,2-de>-1,4-benzoxazin-9-ol

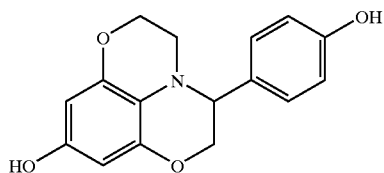

Compound 6a:

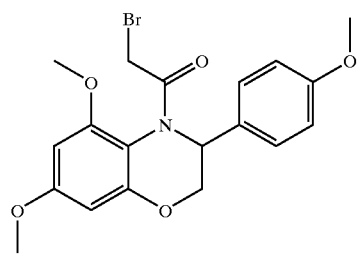

To a solution of compound 1b (124 mg, 0.42 mmol) and triethylamine (1 ml) in anhydrous $CH_2Cl_2$ (2 ml), was added α-bromoacetyl bromide (60 μl, 0.69 mmol) at −20° C. under nitrogen. The reaction mixture was allowed to stir for 1.5 hours. Thereafter, the mixture was diluted with EtOAc (30 ml), washed with 1N HCl (15 ml), brine (15 ml), dried over $MgSO_4$, concentrated and flash chromatographed (silica gel, 25% EtOAc/Hexanes) to afford 97 mg (55%) of compound 6a as an off-white foam.

HPLC retention time=3.21 min. LC/MS (ESI) $(M+H)^+$ =421. $^1H$ NMR ($CDCl_3$, 400 MHz) δ 7.19 (d, J=8.2 Hz, 2H), 6.74 (d, J=8.2 Hz, 2H), 6.03 (m, 3H), 4.81 (d, J=11.8 Hz, 1H), 4.51 (d, J=11.8 Hz, 1H), 4.05 (ABq, J=10.5 Hz, 2H), 3.77 (s, 3H), 3.73 (s, 3H), 3.71 (s, 3H).

Compound 6b:

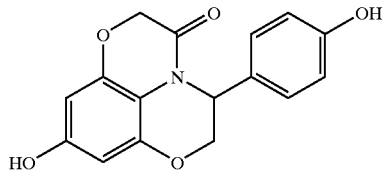

Compound 6a (97 mg, 0.23 mmol) was dissolved in anhydrous $CH_2Cl_2$ (2 ml) and treated with $BBr_3$ (300 μl, 3.17 mmol) at −20° C. The reaction mixture was slowly warmed overnight to rt. Thereafter, the reaction was quenched by dropwise addition of a saturated $NaHCO_3$ solution (15 ml). The resulting gelatinous mixture was partitioned between EtOAc/Sat. $NaHCO_3$. The EtOAc layers were washed with brine (15 ml), dried over $MgSO_4$, concentrated and flash chromatographed (silica gel, 66% to 80% EtOAc/Hexanes) to afford 55 mg (80% for two steps) of cyclized compound 6b.

To a solution of compound 6b (55 mg, 0.18 mmol) in THF (3 ml) was added lithium aluminum hydride (1.8 ml, 1M solution in THF, 1.8 mmol) at −70° C. under argon. The resulting reaction mixture was allowed to warm to rt and stir for three days. The reaction mixture was quenched by addition of 1N HCl (1 ml) and stirred for 20 min. Subsequently, the reaction mixture was filtered through Celite® and the filtrate was partitioned between EtOAc/$H_2O$. The EtOAc layers were washed with brine (15 ml), dried over $MgSO_4$, concentrated and flash chromatographed (silica gel, 60% EtOAc/Hexanes) to afford 2.9 mg (5%) of the title compound.

HPLC retention time=2.20 min. LC/MS (ESI) $(M+H)^+$ =285. $^1H$ NMR ($CD_3OD$, 400 MHz) δ 7.16 (d, J=7.9 Hz, 2H), 6.79 (d, J=7.9 Hz, 2H), 5.84 (d, J=1.8 Hz, 2H), 4.11–4.24 (m, 4H), 3.77 (m, 1H), 2.91 (d, J=9.2 Hz, 2H), 2.59 (m, 2H).

EXAMPLE 7

(R,S) 3-(4-hydroxyphenyl)-2-methyl-2H-1,4-benzoxazine-5,7-diol

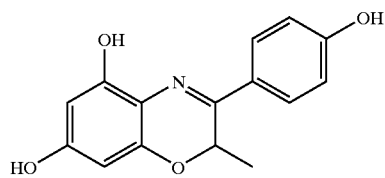

Compound 7a:

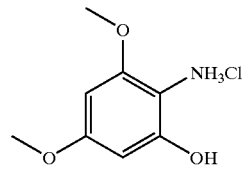

A mixture of 2-nitro-3,5-dimethoxyphenol (212 mg, 1.06 mmol) and 10% palladium on carbon (21.2 mg) in MeOH (2 ml) was maintained under an atmosphere of hydrogen overnight. The catalyst was filtered and to the filtrate was added 1N HCl in ether (1.5 ml). Removal of solvent gave compound 7a as a slight yellowish solid (220 mg, 100%).

HPLC retention time=0.53 min. LC/MS (ESI) $(M+H)^+$ =170.

Compound 7b:

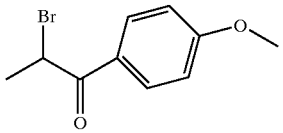

To a solution of 4-methoxypropiophenone (1.64 g, 10 mmol) in chloroform (9 ml) was added dropwise a solution of bromine (556 μl, 10.8 mmol) in $CHCl_3$ (1.8 ml) through an addition funnel. After one hour, the reaction mixture was diluted with $CH_2Cl_2$ (100 ml), washed with sat. $NaHCO_3$, brine, dried over $MgSO_4$ and concentrated to give compound 7b (2.31 g, 95%) as a white solid which was used in the next step without further purification.

HPLC retention time=2.92 min. LC/MS (ESI) (M+H)$^+$ =243.

Compound 7c:

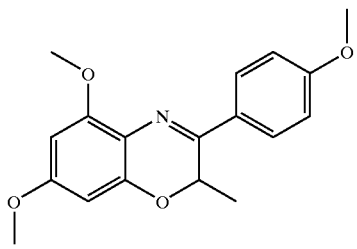

To a suspension of compound 7a (718 mg, 3.5 mmol) in acetone (40 ml) was added cesium carbonate (3.42 g, 10.5 mmol). The resulting dark red mixture was stirred at rt for 10 min, after which compound 7b (932 mg, 3.9 mmol) was added. After one hour, the reaction mixture was filtered. The filtrate was concentrated and flash chromatographed (silica gel, 25% EtOAc/Hexanes) to afford 650 mg (60%) of compound 7c as a yellow foam.

HPLC retention time=3.37 min. LC/MS (ESI) (M+H)$^+$ =314. $^1$H NMR (CDCl$_3$, 400 MHz) δ 7.91 (d, J=8.8 Hz, 2H), 6.94 (d, J=8.8 Hz, 2H), 6.17 (d, J=2.6 Hz, 1H), 6.13 (d, J=2.6 Hz, 1H), 5.47 (q, J=6.8 Hz, 1H), 3.94 (s, 3H), 3.86 (s, 3H), 3.81 (s, 3H), 1.38 (d, J=6.8 Hz, 3H).

Per the procedure described for the preparation of the Example 2 compound, compound 7c (51 mg, 0.163 mmol) was demethylated to provide the title compound (34 mg, 77%) as an orange-colored foam.

HPLC retention time=2.06 min. LC/MS (ESI) (M+H)$^+$ =272. $^1$H NMR (CD$_3$OD, 400 MHz) δ 7.09 (d, J=8.8 Hz, 2H), 6.85 (d, J=8.8 Hz, 2H), 5.98 (d, J=2.2 Hz, 1H), 5.86 (d, J=2.2 Hz, 1H), 5.50(q, J=6.6 Hz, 1H), 1.31 (d, J=6.6 Hz, 3H).

The enantiomers of the title compound were separated by chiral preparative HPLC using a CHIRALPAK® AD column (5×50 cm) with 40% of isopropanol/hexane as an eluent at a flow rate of 75 ml/min to provide enantiomer A and enantiomer B.

HPLC retention time of enantiomer A=8.4 min. (Chiralcel AD column (4.6×250 mm) with 40% of isopropanol/hexane as an eluent at a flow rate of 1 ml/min; detector wavelength=220 nm) LC/MS (ESI) (M+H)$^+$=272. HPLC retention time of enantiomer B=13.7 min. LC/MS (ESI) (M+H)$^+$ =272.

EXAMPLE 8

2-ethyl-3-(4-hydroxyphenyl)-2H-1,4-benzoxazin-7-ol

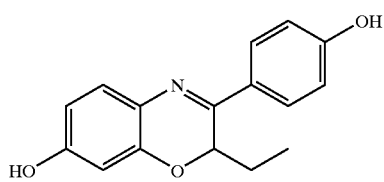

Compound 8a:

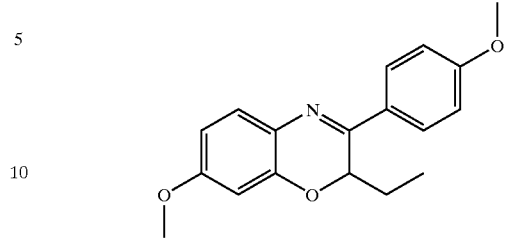

To a suspension of 2-hydroxy-4-methoxyaniline (1.0 g, 5.7 mmol) in acetone (10 ml) was added cesium carbonate (7 g, 21.5 mmol), thereafter forming a dark red mixture. After stirring the mixture at rt for 10 min, 2-bromo-4'-methoxybutyrophenone (1.46 g, 5.7 mmol) [prepared according to the procedure described for compound 7b] was added. After three hours, the reaction mixture was filtered and the filtrate was concentrated and flash chromatographed (silica gel, 17% EtOAc/hexanes) to afford compound 8a as a yellow foam in quantitative yield.

HPLC retention time=3.63 min. LC/MS (ESI) (M+H)$^+$ =298. $^1$H NMR (CDCl$_3$, 400 MHz) δ 7.88 (d, J=8.9 Hz, 2H), 6.96 (d, J=8.9 Hz, 2H), 7.30 (d, J 8.6 Hz, 1H), 6.55 (dd, J=8.6, 2.7 Hz, 1H), 6.49 (d, J=2.7 Hz, 1H), 5.21 (dd, J=10.2, 3.4 Hz, 1H), 3.86 (s, 3H), 3.81 (s, 3H), 1.50–1.90 (m, 2H), 1.04 (t, J=7.3 Hz, 3H).

Per the procedure described for the preparation of the Example 2 compound, compound 8a (111 mg, 0.37 mmol) was demethylated to provide the title compound (50.6 mg, 51%) as an orange-colored foam.

HPLC retention time=2.36 min. $^1$H NMR (CD$_3$OD, 400 MHz) δ 7.80 (d, J=8.9 Hz, 2H), 6.89 (d, J=8.9 Hz, 2H), 7.15 (d, J=8.5, 1H), 6.45 (dd, J=8.5, 2.6, 1H), 6.36(d, J=2.6 Hz, 1H), 5.30 (dd, J=10.1, 3.6 Hz, 1H), 1.72–1.81 (m, 1H), 1.52–1.58 (m, 1H), 1.03 (t, J=7.4 Hz, 3H).

The enantiomers of the title compound were separated by chiral preparative HPLC using a CHIRALPAK® AD column (5×50 cm) with 10% of isopropanol/hexane as an eluent at a flow rate of 75 ml/min to provide enantiomer A and enantiomer B.

HPLC retention time of enantiomer A=13.9 min. (Chiralcel AD column (4.6×250 mm) with 10% of isopropanol/ hexane as an eluent at a flow rate of 1 ml/min; detector wavelength=220 nm) LC/MS (ESI) (M+H)$^+$=270. HPLC retention time of enantiomer B=16.6 min. LC/MS (ESI) (M+H)$^+$=270.

EXAMPLE 9

2-ethyl-3-(4-hydroxyphenyl)-5-methyl-2H-1,4-benzoxazin-7-ol

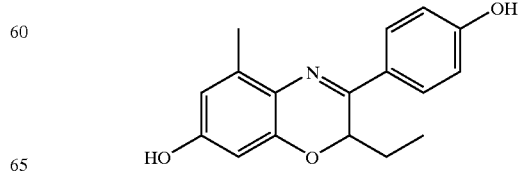

Compound 9a:

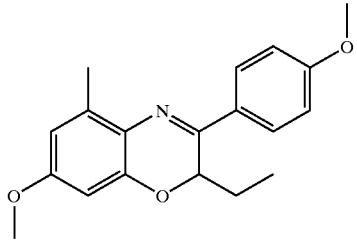

To a pinkish suspension of 2-hydroxy-4-methoxy-6-methylaniline hydrochloric acid salt (78 mg, 0.41 mmol) [prepared according to the procedure for compound 7a] in acetone (10 ml) was added cesium carbonate (424 mg, 1.3 mmol) to produce a pale yellow solution. The resulting solution was stirred at rt for 10 min, after which 2-bromo-4'-methoxybutyrophenone (106 mg, 0.41 mmol) was added. The reaction mixture was refluxed for six hours, then cooled to rt and filtered. The filtrate was concentrated and flash chromatographed (silica gel, 11% EtOAc/hexanes) to afford 103 mg of compound 9a (81%) as a yellow oil.

HPLC retention time=4.03 min. $^1$H NMR (CDCl$_3$, 400 MHz) δ 7.91 (d, J=8.9 Hz, 2H), 6.96 (d, J=8.9 Hz, 2H), 6.43 (d, J=2.6 Hz, 1H), 6.34 (d, J=2.6 Hz, 1H), 5.18 (dd, J=10.3, 3.5 Hz, 1H), 3.87 (s, 3H), 3.79 (s, 3H), 2.51 (s, 3H), 1.50–1.90 (m, 2H), 1.04 (t, J=7.3 Hz, 3H).

Per the procedure described for the preparation of the Example 2 compound, compound 9a (103 mg, 0.331 mmol) was demethylated to provide the title compound (27.5 mg, 29%) as an orange-colored foam.

HPLC retention time=2.83 min. $^1$H NMR (CD$_3$OD, 400 MHz) δ 7.94 (d, J=8.8 Hz, 2H), 6.96 (d, J=8.8 Hz, 2H), 6.39 (d, J=2.5 Hz, 1H), 6.29(d, J=2.56 Hz, 1H), 5.51 (dd, J=10.2, 3.5 Hz, 1H), 2.46 (s, 3H), 1.77–1.84 (m, 1H), 1.54–1.58 (m, 1H), 1.03 (t, J 7.3 Hz, 3H). LC/MS (ESI) (M+H)$^+$=284.

EXAMPLES 10 to 36

Examples 10 to 36 set out in the following table were prepared by employing the procedures described for Examples 1 to 9 and reaction Schemes 1 to 4 above.

TABLE 1

| Example | Z | Y | R$^1$ | R$^2$ | R$^4$ | R$^3$ | Method |
|---|---|---|---|---|---|---|---|
| 10[a] | H | Ac | H | H | H | 5-OMe | Ex. 2 |
| 11 | H | Ac | H | H | H | 5-OH | Ex. 2 |
| 12 | H | i-PrCO | H | H | H | 5-OH | Ex. 2 |
| 13 | H | n-PrCO | H | H | H | 5-OH | Ex. 2 |
| 14 | H | PhCO | H | H | H | 5-OH | Ex. 2 |
| 15 | H | EtNHCO | H | H | H | 5-OH | Ex. 4 |
| 16 | | bond | H | H | H | 5-OH | Ex. 7 |
| 17 | H | MeOCO | H | H | H | 5-OH | Ex. 4 |
| 18 | H | EtOCO | H | H | H | 5-OH | Ex. 4 |
| 19 | H | EtCO | H | Me | H | 5-OH | Ex. 2 |
| 20 | H | MeSCO | H | H | H | 5-OH | Ex. 4 |
| 21 | H | MeCO | H | Me | H | 5-OH | Ex. 2 |
| 22 | | bond | H | H | H | H | Ex. 7 |
| 23 | H | Me$_2$NCO | H | H | H | 5-OH | Ex. 4 |
| 24 | H | EtCO | H | H | H | H | Ex. 2 |
| 25 | | bond | H | Me | H | H | Ex. 7 |
| 26 | H | EtCO | H | Me | H | H | Ex. 2 |
| 27 | | bond | H | Et | H | 5-OH | Ex. 7 |
| 28[a] | | bond | H | Et | 3'-Br | 5-OH | Ex. 7 |
| 29 | | bond | H | —CH$_2$CH$_2$— | | H | Ex. 7 |
| 30 | | bond | H | —CH$_2$— | | H | Ex. 7 |
| 31 | | bond | H | Pr | H | H | Ex. 7 |
| 32 | | bond | Me | Me | H | H | Ex. 7 |
| 33 | | bond | Me | Me | H | 5-OH | Ex. 7 |
| 34 | | bond | H | Me | H | 5-Me | Ex. 9 |
| 35 | | bond | H | Et | H | 8-Me | Ex. 9 |
| 36 | | bond | H | H | H | 8-Me | Ex. 9 |

[a]Indicates compounds were isolated as intermediates or side products from final demethylation reactions.

What is claimed is:
1. A compound of the formula I

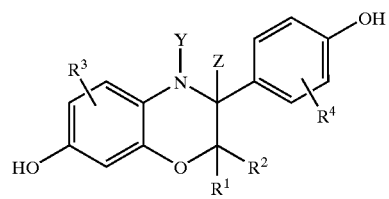

wherein
R$^1$ and R$^2$ are each independently selected from the group consisting of hydrogen, substituted or unsubstituted alkyl, substituted or unsubstituted aryl, substituted or unsubstituted cycloalkylalkyl, substituted or unsubstituted arylalkyl and hydroxyalkyl, or R$^2$ together with R$^4$ may independently be cyclized to form —(CH$_2$)$_n$— where n=1, 2, or 3;

R$^3$ is selected from the group consisting of OH, halo, CF$_3$, CN, substituted alkyl, substituted or unsubstituted alkenyl, substituted or unsubstituted alkynyl and alkoxy;

R$^4$ is selected from the group consisting of hydrogen, substituted or unsubstituted alkyl, halo, OH and alkoxy;

Z is hydrogen, or Y and Z can together form a bond;

Y, where Z is H, is selected from the group consisting of hydrogen, substituted or unsubstituted alkyl, COR$^5$, CSR$^5$, SO$_2$R$^5$, CONR$^6$R$^7$, COOR$^8$ and COSR$^9$, or Y together with R$^3$ may form a six membered heterocyclic ring containing —OCH$_2$CH$_2$— or —OCH$_2$CO—;

R$^5$ is hydrogen, substituted or unsubstituted alkyl or substituted or unsubstituted aryl;

R$^6$ and R$^7$ are each independently hydrogen, substituted or unsubstituted alkyl or substituted or unsubstituted aryl; and R$^8$ and R$^9$ are each independently substituted or unsubstituted alkyl or substituted or unsubstituted aryl;

or all prodrug esters, or pharmaceutically acceptable salts and stereoisomers thereof;

in each of the above groups, where employed, the term "substituted alkyl" refers to an alkyl group substituted with one or more functional groups selected from hydroxyl, bromo, fluoro, chloro, iodo, mercapto, cyano, alkylthio, heterocyclyl, aryl, heteroaryl, carboxyl, alkyl, alkenyl, nitro, amino, alkoxyl, or amido;

where employed, the term "substituted alkenyl" refers to an alkenyl group optionally substituted with substituents as described for alkyl;

where employed, the term "substituted alkynyl" refers to an alkynyl group optionally substituted with 1 or more substituents as described for alkyl;

where employed, the term "substituted aryl" refers to an aryl group optionally substituted with 1 or more functional groups, selected from halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, and/or any of the alkyl substituents set out herein;

where employed, the term "substituted cycloalkyl" refers to a cycloalkyl group optionally substituted with substituents as described for alkyl and/or aryl;

where employed, the term "substituted cycloalkylalkyl" refers to a cycloalkylalkyl group optionally substituted with 1 or more substituents as described for alkyl and/or aryl;

where employed, the term "substituted arylalkyl" refers to an arylalkyl group optionally substituted with 1 or more substituents as described for alkyl and/or aryl; and where employed, the term "alkoxy" denotes —OR, wherein R is alkyl.

2. A compound having the structure

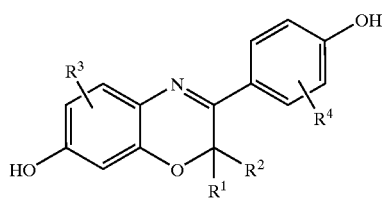

wherein
R$^1$ and R$^2$ are each independently selected from the group consisting of hydrogen, substituted or unsubstituted alkyl, substituted or unsubstituted aryl, substituted or unsubstituted cycloalkylalkyl, substituted or unsubstituted arylalkyl and hydroxyalkyl, or R$_2$ together with R$^4$ may independently be cyclized to form —(CH$_2$)$_n$— where n=1,2, or 3;

R$^3$ is selected from the group consisting of hydrogen, OH, halo, CF$_3$, CN, substituted or unsubstituted alkyl, substituted or unsubstituted alkenyl, substituted or unsubstituted alkynyl and alkoxy;

R$_4$ is selected from the group consisting of hydrogen, substituted or unsubstituted alkyl, halo, OH and alkoxy;

in each of the above groups, where employed, the term "substituted alkyl" refers to an alkyl group optionally substituted with one or more functional groups selected from hydroxyl, bromo, fluoro, chloro, iodo, mercapto, cyano, alkylthio, heterocyclyl, aryl, heteroaryl, carboxyl, alkyl, alkenyl, nitro, amino, alkoxyl, or amido;

where employed, the term "substituted alkenyl" refers to an alkenyl group optionally substituted with substituents as described for alkyl;

where employed, the term "substituted alkynyl" refers to an alkynyl group optionally substituted with 1 or more substituents as described for alkyl;

where employed, the term "substituted aryl" refers to an aryl group optionally substituted with 1 or more functional groups, selected from halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, and/or any of the alkyl substituents set out herein;

where employed, the term "substituted cycloalkyl" refers to a cycloalkyl group optionally substituted with substituents as described for alkyl and/or aryl;

where employed, the term "substituted cycloalkylalkyl" refers to a cycloalkylalkyl group optionally substituted with 1 or more substituents as described for alkyl and/or aryl;

where employed, the term "substituted arylalkyl" refers to an arylalkyl group optionally substituted with 1 or more substituents as described for alkyl and/or aryl; and where employed, the term "alkoxy" denotes —OR, wherein R is alkyl.

3. The compound as defined in claim 2 wherein
R$^1$ is alkyl;
R$^2$ is hydrogen;
R$^3$ is selected from the group consisting of hydrogen, alkyl and OH; and
R$^4$ is selected from the group consisting of hydrogen, alkyl, halo, OH and alkoxy.

4. The compound as defined in claim 2 wherein
R$^1$ is alkyl;
R$^2$ is hydrogen;
R$^3$ is alkyl or OH; and
R$^4$ is selected from the group consisting of hydrogen, alkyl, halo, OH and alkoxy.

5. A pharmaceutical composition comprising a compound as defined in claim 1 and a pharmaceutically acceptable carrier therefor.

6. A pharmaceutical composition capable of modulating the function of an estrogen receptor beta (ERβ), comprising a compound of formula I

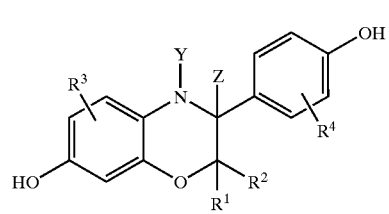

wherein
R$^1$ and R$^2$ are each independently selected from the group consisting of hydrogen, substituted or unsubstituted alkyl, substituted or unsubstituted aryl, substituted or unsubstituted cycloalkylalkyl, substituted or unsubstituted arylalkyl and hydroxyalkyl, or R$^2$ together with R$^4$ may independently be cyclized to form —(CH$_2$)$_n$— where n=1, 2, or 3;

R$^3$ is selected from the group consisting of OH, halo, CF$_3$, CN, substituted alkyl, substituted or unsubstituted alkenyl, substituted or unsubstituted alkynyl and alkoxy;

$R^4$ is selected from the group consisting of hydrogen, substituted or unsubstituted alkyl, halo, OH and alkoxy;

Z is hydrogen, or Y and Z can together form a bond;

Y, where Z is H, is selected from the group consisting of hydrogen, substituted or unsubstituted alkyl, $COR^5$, $CSR^5$, $SO_2R^5$, $CONR^6R^7$, $COOR^8$ and $COSR^9$, or Y together with $R^3$ may form a six membered heterocyclic ring containing —$OCH_2CH_2$— or —$OCH_2CO$—;

$R^5$ is hydrogen, substituted or unsubstituted alkyl or substituted or unsubstituted aryl;

$R^6$ and $R^7$ are each independently hydrogen, substituted or unsubstituted alkyl or substituted or unsubstituted aryl; and $R^8$ and $R^9$ are each independently substituted or unsubstituted alkyl or substituted or unsubstituted aryl;

or all prodrug esters, pharmaceutically acceptable salts and stereoisomers thereof and a pharmaceutically acceptable carrier;

in each of the above groups, where employed, the term "substituted alkyl" refers to an alkyl group substituted with one or more functional groups selected from hydroxyl, bromo, fluoro, chloro, iodo, mercapto, cyano, alkylthio, heterocyclyl, aryl, heteroaryl, carboxyl, alkyl, alkenyl, nitro, amino, alkoxyl, or amido;

where employed, the term "substituted alkenyl" refers to an alkenyl group optionally substituted with substituents as described for alkyl;

where employed, the term "substituted alkynyl" refers to an alkynyl group optionally substituted with 1 or more substituents as described for alkyl;

where employed, the term "substituted aryl" refers to an aryl group optionally substituted with 1 or more functional groups, selected from halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, and/or any of the alkyl substituents set out herein;

where employed, the term "substituted cycloalkyl" refers to a cycloalkyl group optionally substituted with substituents as described for alkyl and/or aryl;

where employed, the term "substituted cycloalkylalkyl" refers to a cycloalkylalkyl group optionally substituted with 1 or more substituents as described for alkyl and/or aryl;

where employed, the term "substituted arylalkyl" refers to an arylalkyl group optionally substituted with 1 or more substituents as described for alkyl and/or aryl; and where employed, the term "alkoxy" denotes —OR, wherein R is alkyl.

7. The compound as defined in claim 1 wherein Y is H, substituted or unsubstituted alkyl, $COR^5$, $CSR^5$, $SO_2R^5$, $CONR^6R^7$, $COOR^8$, $COSR^9$ or Y together with $R^3$ may form a six membered heterocyclic ring containing —$OCH_2CH_2$— or —$OCH_2CO$—, wherein substituted alkyl is substituted with one or more functional groups selected from hydroxyl, mercapto, cyano, alkylthio, heterocyclyl, aryl, heteroaryl, alkyl, alkenyl, nitro, amino, alkoxyl or amido.

8. The compound as defined in claim 6 wherein Y is H, substituted or unsubstituted alkyl, $COR^5$, $CSR^5$, $SO_2R^5$, $CONR^6R^7$, $COOR^8$, $COSR^9$ or Y together with $R^3$ may form a six membered heterocyclic ring containing —$OCH_2CH_2$— or —$OCH_2CO$—, wherein substituted alkyl is substituted with one or more functional groups selected from hydroxyl, mercapto, cyano, alkylthio, heterocyclyl, aryl, heteroaryl, alkyl, alkenyl, nitro, amino, alkoxyl or amido.

* * * * *

UNITED STATES PATENT AND TRADEMARK OFFICE
CERTIFICATE OF CORRECTION

PATENT NO. : 7,015,219 B2 Page 1 of 1
APPLICATION NO. : 10/322689
DATED : March 21, 2006
INVENTOR(S) : John K. Dickson et al.

It is certified that error appears in the above-identified patent and that said Letters Patent is hereby corrected as shown below:

In claim 2, column 25, line 45 and 46, "$R_2$ together with $R^4$" should be repalced with -- $R^2$ together with $R^4$ --

Signed and Sealed this

Seventh Day of August, 2007

JON W. DUDAS
*Director of the United States Patent and Trademark Office*